United States Patent
Shi

(10) Patent No.: US 11,462,316 B2
(45) Date of Patent: Oct. 4, 2022

(54) SYSTEMS AND METHODS FOR EVALUATING MEDICAL IMAGE

(71) Applicant: SHANGHAI UNITED IMAGING HEALTHCARE CO., LTD., Shanghai (CN)

(72) Inventor: Yuhang Shi, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 166 days.

(21) Appl. No.: 16/871,070

(22) Filed: May 11, 2020

(65) Prior Publication Data

US 2021/0151170 A1    May 20, 2021

(30) Foreign Application Priority Data

Nov. 14, 2019   (CN) .......................... 201911111585.3

(51) Int. Cl.
| | | |
|---|---|---|
| G16H 30/40 | (2018.01) | |
| G06N 20/10 | (2019.01) | |
| G06K 9/62 | (2022.01) | |
| G06T 7/00 | (2017.01) | |
| G06V 10/75 | (2022.01) | |

(52) U.S. Cl.
CPC ........... *G16H 30/40* (2018.01); *G06K 9/6269* (2013.01); *G06K 9/6278* (2013.01); *G06N 20/10* (2019.01); *G06T 7/0014* (2013.01); *G06V 10/758* (2022.01)

(58) Field of Classification Search
CPC .......................... G06T 7/0012; G06K 9/00288
See application file for complete search history.

(56) References Cited

U.S. PATENT DOCUMENTS

| | | | | |
|---|---|---|---|---|
| 2011/0257919 | A1* | 10/2011 | Reiner | G16H 30/20 702/81 |
| 2017/0372155 | A1 | 12/2017 | Odry et al. | |
| 2019/0244399 | A1 | 8/2019 | Li et al. | |
| 2020/0380669 | A1* | 12/2020 | Wu | G06T 7/0002 |
| 2020/0380675 | A1* | 12/2020 | Golden | G06T 7/0012 |

FOREIGN PATENT DOCUMENTS

| | | |
|---|---|---|
| CN | 103745226 A | 4/2014 |
| CN | 103810287 A | 5/2014 |
| CN | 105913084 A | 8/2016 |
| CN | 106780448 A | 5/2017 |
| CN | 107595312 A | 1/2018 |
| CN | 108364006 A | 8/2018 |
| CN | 109300121 A | 2/2019 |
| CN | 109492700 A | 3/2019 |
| CN | 109727235 A | 5/2019 |
| CN | 110428415 A | 11/2019 |

OTHER PUBLICATIONS

First Office Action in Chinese Application No. 201911111585.3 dated Jan. 27, 2022, 22 pages.

* cited by examiner

*Primary Examiner* — Ross Varndell
(74) *Attorney, Agent, or Firm* — Metis IP LLC

(57) ABSTRACT

The present disclosure relates to systems and methods for evaluating a medical image. The systems and methods may obtain the medical image. The systems and methods may extract a feature of the medical image. The feature may include a histogram of oriented gradients (HOG) feature of the medical image. The systems and methods may determine a degree to which an artifact in the medical image affects recognition of a tissue feature by inputting the feature of the medical image to a determination model.

18 Claims, 10 Drawing Sheets

1000

SYSTEMS AND METHODS FOR EVALUATING MEDICAL IMAGE

CROSS-REFERENCE TO RELATED APPLICATIONS

This application claims priority to Chinese Patent Application No. 201911111585.3 filed on Nov. 14, 2019, the contents of which are incorporated herein by reference.

TECHNICAL FIELD

The present disclosure generally relates to medical image processing, and in particular, to systems and methods for evaluating a medical image.

BACKGROUND

In a medical imaging system, the quality of a medical image acquired by the medical imaging system depends on many factors, such as but not limited to spatial resolution, tissue contrast, signal-to-noise ratio, contrast-to-noise ratio, and image defects. Sometimes an artifact may exist in the medical image and the artifact may affect the quality of the medical image, and further affect the diagnosis or prognosis based on the medical image.

To improve the quality of the medical image to meet various needs, a physician often needs to manually retrieve and observe the medical image to evaluate its quality and determine whether an image should be reacquired. However, human evaluation of image quality can be slow and inefficient, especially when a plurality of medical images are needed or produced in a single process. For example, a magnetic resonance scan of a human body often generates at least twenty, most likely more, images. It would simply be too time-consuming and demanding for a physician evaluate and determine the image quality for all the images.

Therefore, it is desirable to provide methods and systems for evaluating the medical images efficiently.

SUMMARY

According to an aspect of the present disclosure, a system for evaluating a medical image is provided. The system may include at least one storage device including a set of instructions and at least one processor configured to communicate with the at least one storage device. When executing the set of instructions, the at least one processor may be configured to direct the system to perform the following operations. The system may obtain the medical image. The system may extract a feature of the medical image. The feature may include a histogram of oriented gradients (HOG) feature of the medical image. The system may determine a degree to which an artifact in the medical image affects recognition of a tissue feature by inputting the feature of the medical image to a determination model.

In some embodiments, the extracting the HOG feature of the medical image may include calculating a gradient of each pixel in the medical image, segmenting the medical image into a plurality of cell units, each of the plurality of cell units including a same count of pixels, counting a HOG feature of each of the plurality of cell units based on the gradient of each pixel in each of the plurality of cell units, counting a HOG feature of each of the plurality of cell units based on the gradient of each pixel in each of the plurality of cell units, combining the plurality of cell units into one or more blocks according to a predetermined number, and counting a HOG feature of each of the one or more blocks based on one or more HOG features of one or more cell units included in each of the one or more blocks, and obtaining a HOG feature of the medical image by stitching the HOG features of the one or more blocks.

In some embodiments, the operations may further include normalizing the HOG feature of each of the one or more blocks before stitching the HOG features of the one or more blocks.

In some embodiments, the operations may further include a process for obtaining the determination model. The process may include obtaining a plurality of sample medical images and a label of each of the plurality of sample medical images, wherein the label represents a degree to which an artifact in each of the plurality of sample medical images affects the tissue feature recognition, extracting a feature of each of the plurality of sample medical images, and obtaining the determination model by training a preliminary determination model based on the extracted feature and the label of each of the plurality of sample medical images.

In some embodiments, the process may further include preprocessing each of the plurality of sample medical images. The preprocessing may include regularizing a size of each of the plurality of sample medical images and/or standardizing a color of each of the plurality of sample medical images.

In some embodiments, the operations may further include obtaining additional determination models corresponding to different tissue types. Each of the determination models may be obtained based on a plurality of sample medical images including a tissue type corresponding to each of the determination models.

In some embodiments, the operations may further include determining a tissue type included in the medical image, obtaining a determination model corresponding to the tissue type, and determining the degree to which the artifact in the medical image affects recognition of the tissue feature by inputting the feature of the medical image to the determination model corresponding to the tissue type.

In some embodiments, the feature may further include a gender and an age of a user from whom the medical image is acquired, and/or a tissue type of the medical image.

In some embodiments, the determination model may include a support vector machine model, a logistic regression model, a naive Bayes classification model, a decision tree model, or a deep learning model.

According to another aspect of the present disclosure, a system for medical image acquisition may include at least one storage device including a set of instructions and at least one processor configured to communicate with the at least one storage device. When executing the set of instructions, the at least one processor may be configured to direct the system to perform the following operations. The system may acquire a first medical image and conduct a determination process in real time. The determination process may include extracting a HOG feature of the first medical image, determining a degree to which an artifact in the medical image affects recognition of tissue feature by inputting the HOG feature of the first medical image to a determination model, and determining whether the degree satisfies a preset condition, and acquiring a second medical image in response to a determination that the degree does not satisfy the preset condition.

In some embodiments, the determination model may be a shallow learning model. The shallow learning model may include a support vector machine model, a logistic regression model, a naive Bayes classification model, or a decision tree model.

According to yet another aspect of the present disclosure, a method for evaluating a medical image may include obtaining the medical image, extracting a feature of the medical image, the feature including a histogram of oriented gradients (HOG) feature of the medical image; and determining a degree to which an artifact in the medical image affects recognition of a tissue feature by inputting the feature of the medical image to a determination model.

In some embodiments, the method may further include normalizing the HOG feature of each of the one or more blocks before stitching the HOG features of the one or more blocks.

In some embodiments, the method may further include preprocessing each of the plurality of sample medical images. The preprocessing may include regularizing a size of each of the plurality of sample medical images and/or standardizing a color of each of the plurality of sample medical images.

In some embodiments, the method may further include obtaining additional determination models corresponding to different tissue types, wherein each of the determination models is obtained based on a plurality of sample medical images including a tissue type corresponding to each of the determination models.

In some embodiments, the method may further include determining a tissue type included in the medical image, obtaining a determination model corresponding to the tissue type, and determining the degree to which the artifact in the medical image affects recognition of the tissue feature by inputting the feature of the medical image to the determination model corresponding to the tissue type.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise.

It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, sections or assembly of different levels in ascending order. However, the terms may be displaced by another expression if they achieve the same purpose.

Figure 3:
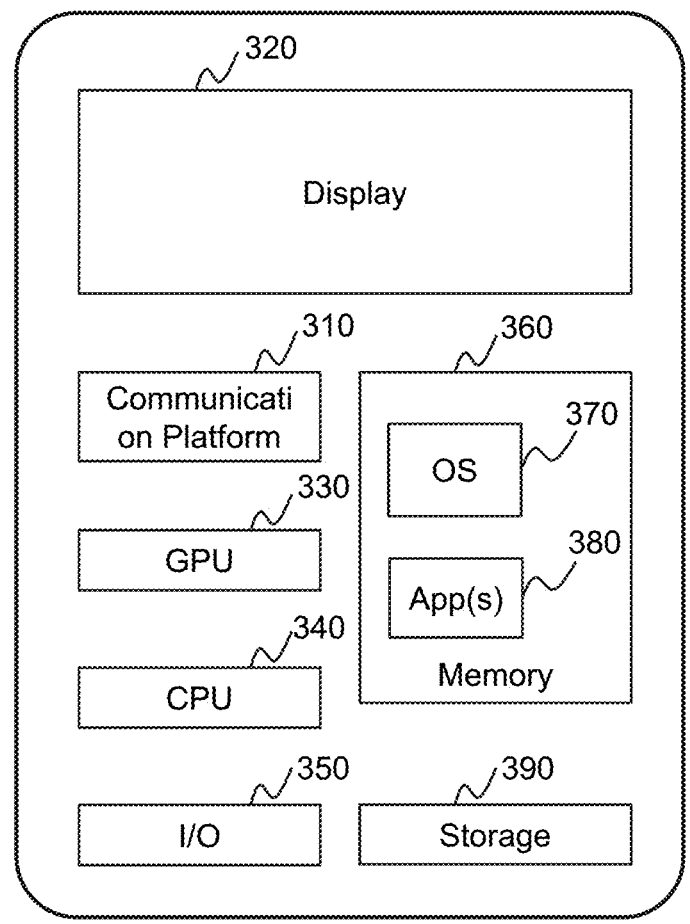
FIG. 3 is a schematic diagram illustrating exemplary hardware and/or software components of a mobile device on which the terminal may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a magnetic resonance imaging (MRI) system. Exemplary MRI systems may include a superconducting magnetic resonance imaging system, a non-superconducting magnetic resonance imaging system, etc. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc. In some embodiments, the medical system may include a treatment system. The treatment system may include a treatment plan system (TPS), image-guide radiotherapy (IGRT), etc. The image-guide radiotherapy (IGRT) may include a treatment device and an imaging device. The treatment device may include a linear accelerator, a cyclotron, a synchrotron, etc., configured to perform a radio therapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc.

An aspect of the present disclosure relates to systems and methods for evaluating a medical image. The systems and methods may obtain the medical image. The systems and methods may extract a feature of the medical image. The feature may include a HOG feature of the medical image. The systems and methods may determine a degree to which an artifact in the medical image affects recognition of a tissue feature by inputting the feature of the medical image to a determination model.

According to some embodiments of the present disclosure, the degree to which an artifact in the medical image affects recognition of a tissue feature may be determined automatically. Compared with a conventional approach that determines the degree to which an artifact in the medical image affects recognition of a tissue feature by manually observing the medical image, the systems and methods of the present disclosure may obviate the need for human intervention, and be insusceptible to human error or subjectivity. Based on the degree to which an artifact in the medical image affects recognition of the tissue feature, the systems and methods of the present disclosure may acquire another medical image in response to that the degree to which the artifact in the medical image affects recognition of the tissue feature does not satisfy a preset condition, thereby improving the quality of the medical image and ensuring the accuracy of a diagnosis.

The beneficial effects of the present disclosure may include, but are not limited to the following beneficial effects. A fully automated evaluation for a medical image without manual evaluation is provided, thereby effectively reducing the workload of a doctor. During the acquiring of the medical image, the medical image may be evaluated in real time, and the medical image that does not meet a need may be reacquired in real time. The process is fully automated without manual intervention. A determination model corresponding to a tissue type may be performed, thereby improve valuation accuracy. Readability of information of the medical image may be increased, which may be convenient for a user to efficiently identify and understand the quality of the medical image, thereby assisting in making a scan decision.

Figure 1:
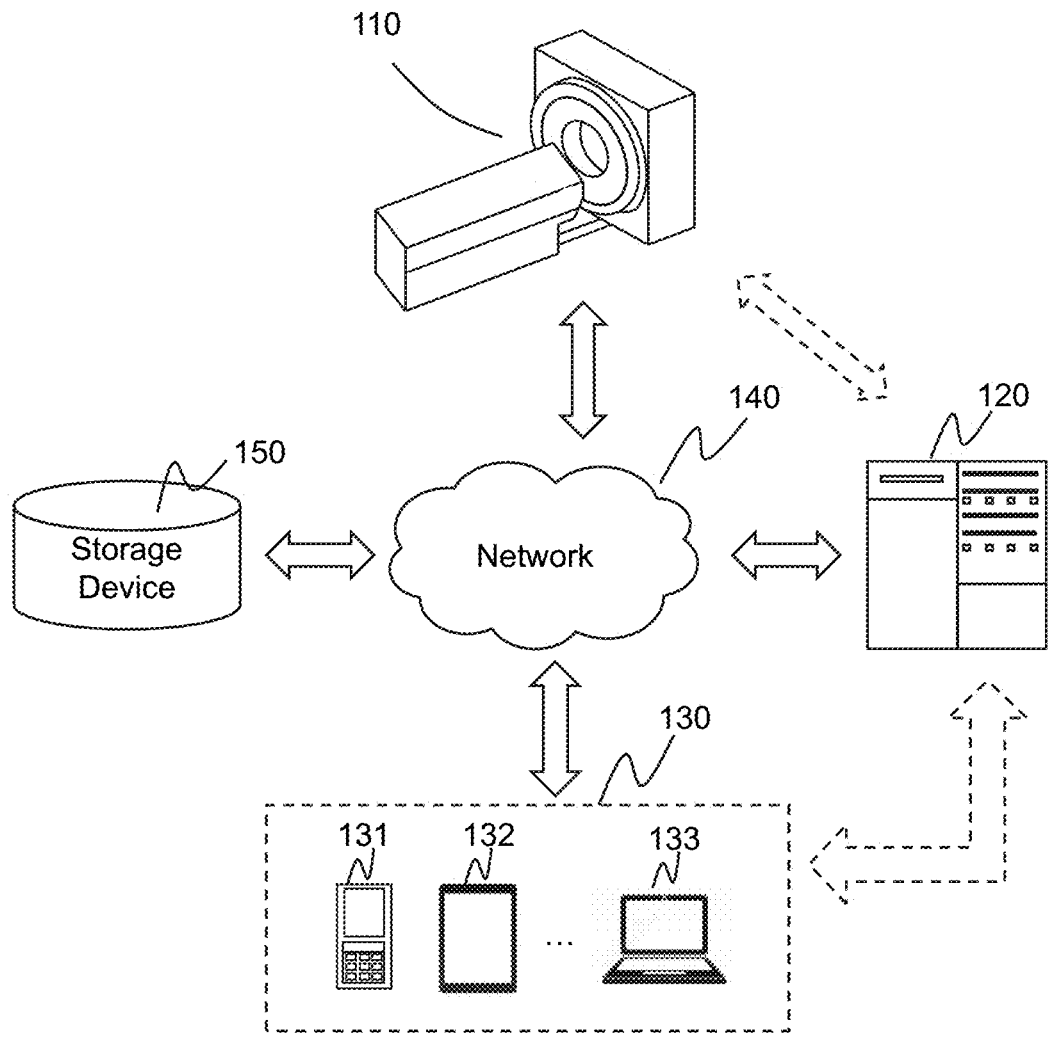
FIG. 1 is a schematic diagram illustrating an exemplary medical image acquisition system 100 according to some embodiments of the present disclosure.

FIG. 1 is a schematic diagram illustrating an exemplary medical image acquisition system 100 according to some embodiments of the present disclosure. As shown in FIG. 1, the medical image acquisition system 100 may include an imaging device 110, a processing device 120, one or more terminals 130, a network 140, and a storage device 150. The one or more components in the medical image acquisition system 100 may be connected in various ways. Merely by way of example, the imaging device 110 may be connected to the processing device 120 through the network 140. As another example, the imaging device 110 may be connected to the processing device 120 directly as indicated by the bi-directional arrow in dotted lines linking the imaging device 110 and the processing device 120. As still another example, the storage device 150 may be connected to the processing device 120 directly or through the network 140. In some embodiments, the medical image acquisition system 100 may include, but is not limited to a computed tomography (CT) system, a computed tomography angiography (CTA) system, a positron emission tomography (PET) system, a single photon emission computed tomography (SPECT) system, a magnetic resonance imaging (MRI)

system, a digital subtraction angiography (DSA) system, an ultrasound scan (US system), a thermal tomography (TTM) system, etc.

In some embodiments, the imaging device 110 may acquire data by scanning a target object. The target object may include an organ, an organism, an object, an injury site, a tumor, or the like, or any combination thereof. For example, the target object may include the head, the chest cavity, the abdomen, the organs, the bones, and the blood vessels, or the like, or any combination thereof. The acquired data by the imaging device 110 may include medical image data. The medical image data may include two-dimensional (2D) image data and/or three-dimensional (3D) image data. In the 2D medical image data, the most subtle distinguishable element may be a pixel. In the 3D medical image data, the most subtle distinguishable element may be a voxel. In the 3D medical image data, an image may include a series of 2D slices or 2D tomography. A point (or element) in an image can be called a voxel in a three-dimensional image and a pixel in a two-dimensional tomographic image in which it is located. "Voxel" and/or "pixel" are for convenience of description only, and do not limit the 2D and/or 3D images accordingly.

The processing device 120 may process data and/or information obtained from the imaging device 110, the terminal(s) 130, the network 140, and/or the storage device 150. For example, the processing device 120 may obtain the medical image from the imaging device 110 to extract feature(s) (e.g., feature(s) of a user to which the medical image belongs, a gradient feature of pixels) of the medical image. As another example, the processing device 120 may determine a degree to which an artifact in the medical image affects recognition of a tissue feature. In some embodiments, the processing of the data and/or information may include data acquisition, classification, filtering, conversion, calculation, display, or the like, or any combination thereof. The processing device 120 may transmit the processed data to the storage device 150 for storage, or to terminal(s) 130. For example, the processing device 120 may process the image data and transmit the processed image data to the terminal(s) 130 for display.

In some embodiments, the processing device 120 may include, but is not limited to a Central Processing Unit (CPU), an Application Specific Integrated Circuit (ASIC), an Application Specific Instruction Set Processor (ASIP), a Physics Processing Unit (PPU), a Digital Processing Processor (DSP), a Field-Programmable Gate Array (FPGA), a Programmable Logic Device (PLD), a processor, a microprocessor, a controller, a microcontroller, or the like, or any combination thereof.

It should be noted that the processing device 120 may exist in the medical image acquisition system 100, or a corresponding function of the processing device 120 may be completed through a cloud platform. The cloud platform may include, but is not limited to a storage cloud platform mainly for storing data, a computing cloud platform mainly for processing data, and a comprehensive cloud platform for storing and processing data. The cloud platform used in the medical image acquisition system 100 may be a public cloud, a private cloud, a community cloud, or a hybrid cloud. For example, according to actual needs, the medical image(s) acquired by the medical image acquisition system 100 may be simultaneously calculated and/or stored by the cloud platform and the local processing module and/or the medical image acquisition system 100.

The terminal(s) 130 may receive, send, and/or display data and/or information. In some embodiments, the terminal(s) 130 may have a portion of or all of the functions of the processing device 120. For example, the terminal(s) 130 may further process a processing result of the processing device 120 or display data processed by the processing device 120. In some embodiments, the terminal(s) 130 and the processing device 120 may be integrated into a single device. The integrated single device can implement the functions of the processing device 120 and the terminal(s) 130 simultaneously. In some embodiments, the terminal(s) 130 may include an input device, an output device, or the like, or any combination thereof. The input device may include, but is not limited to a character input device (e.g., a keyboard), an optical reading device (e.g., an optical marker reader, an optical character reader), a graphic input device (e.g., a mouse, a joystick, a light pen), an image input device (e.g., a camera, a scanner, a fax machine), an analog input device (e.g., a language analog-to-digital conversion recognition system), or the like, or any combination thereof. The output device may include, but is not limited to, a display device, a printing device, a plotter, an image output system, a voice output system, a magnetic recording device, or the like, or any combination thereof. In some embodiments, the terminal(s) 130 may have both input and output functions, such as a desktop computer, a notebook, a smart-phone, a tablet computer, a personal digital assistant (PDA), or the like. In some embodiments, the terminal(s) 130 may include a mobile device 131, a tablet computer 132, a laptop computer 133, or the like, or any combination thereof.

The network 140 may implement communication of the medical image acquisition system 100. For example, the network 140 may receive information from external of the medical image acquisition system 100 or send information to the external of the medical image acquisition system 100. In some embodiments, the imaging device 110, the terminal(s) 130, the processing device 120, and the storage device 150 may access the network 140 through a wired connection, a wireless connection, or a combination thereof. For example, the processing device 120 may obtain a user instruction from the terminal(s) 130 through the network 140. The network 140 may be a single network or a combination of multiple networks. The network 140 may include but is not limited to a local area network, a wide area network, a public network, a dedicated network, a wireless local area network, a virtual network, a metropolitan area network, a public switched telephone network, or the like, or any combination thereof. In some embodiments, the network 140 may include one or more network access points, such as a wired or wireless access point, a base station, or a network switching point. Through the access point(s), a data source may be connected to the network 140, and information may be transmitted through the network 140.

The storage device 150 may be configured on a device having a storage function. The storage device 150 may store data collected from the imaging device 110 (e.g., a medical image captured by the imaging device 110) and/or various data generated during the operation of the processing device 120 (e.g., a feature of the medical image, a model parameter, etc.). The storage device 150 may also store data (user input data) input through terminal(s) 130. The storage device 150 may be local or remote. In some embodiments, the storage device 150 may be configured in the processing device 120. The storage device 150 may include a hierarchical database, a network database, a relational database, or the like, or any combination thereof. The storage device 150 may digitize the information and then use a storage device such as an electric storage device, a magnetic storage device, or an optical storage device to store the information. The storage device 150 may be used to store various information, such as programs, data, and the like. The storage device 150 may be configured on a device that stores information using electric energy, for example, various memories, a Random Access Memory (RAM), a Read Only Memory (ROM), etc. The RAM may include but not limited to a decatron, a selectron, a delay line memory, a Williams tube, a dynamic random access memory (DRAM), a static random access memory (SRAM), a thyristor random access memory (T-RAM), a zero capacitor random access memory (Z-RAM), or the like, or any combination thereof. The ROM may include but is not limited to a magnetic bubble memory, a magnetic button line memory, a thin film memory, a magnetic plated wire memory, a magnetic-core memory, a magnetic drum memory, a CD-ROM, a hard disk, a tape, an NVRAM (nonvolatile memory), a phase change memory, a magnetic resistance RAM, a ferroelectric RAM, a nonvolatile SRAM, a flash memory, an electronic erasable rewritable ROM, an erasable programmable ROM, a programmable ROM, a mask ROM, a floating gate connected RAM, a Nano-RAM, a race-track memory, a variable resistive RAM and a programmable metallization memory, the like, or any combination thereof.

It should be noted that the above description of the medical image acquisition system 100 is merely for the convenience of description, and not intended to limit the present disclosure to the scope of the embodiments. For persons having ordinary skills in the art, modules may be combined in various ways, or connected with other modules as sub-systems. Various variations and modifications may be conducted under the teaching of the present disclosure. However, those variations and modifications may not depart the spirit and scope of this disclosure. For example, the storage device 150 may be configured in a cloud platform having a data storage function, including but not limited to a public cloud, a private cloud, a community cloud, a hybrid cloud, or the like. As another example, two or more of the imaging device 110, the processing device 120, the terminal(s) 130, the storage device 150 may be directly configured in one device, and communicates with each other without using the network 140. All such modifications are within the protection scope of the present disclosure.

Figure 2:
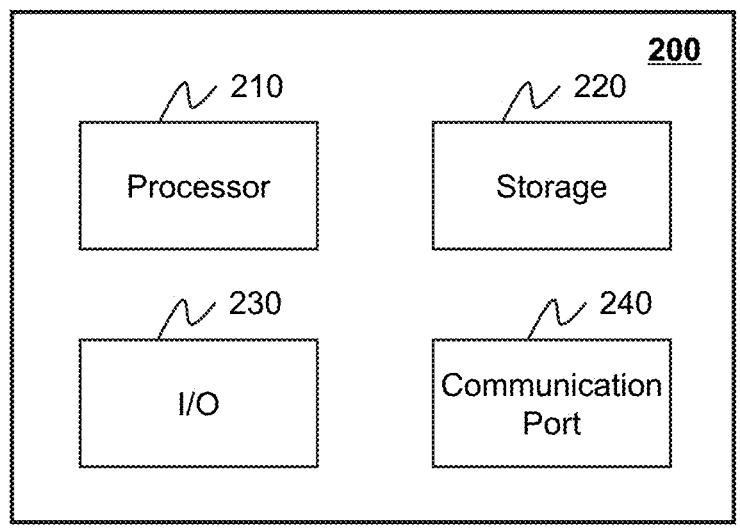
FIG. 2 is a schematic diagram illustrating exemplary hardware and/or software components of a computing device on which the processing device may be implemented according to some embodiments of the present disclosure.

FIG. 2 is a schematic diagram illustrating hardware and/or software components of an exemplary computing device 200 according to some embodiments of the present disclosure. The computing device 200 may be used to implement any component of the medical image acquisition system 100 as described herein. For example, the processing device 120 and/or the terminalS 130 may be implemented on the computing device 200, respectively, via its hardware, software program, firmware, or a combination thereof. Although only one such computing device is shown, for convenience, the computer functions relating to the medical image acquisition system 100 as described herein may be implemented in a distributed fashion on a number of similar platforms, to distribute the processing load.

As illustrated in FIG. 2, the computing device 200 may include a processor 210, a storage 220, an input/output (I/O) 230, and a communication port 240. The processor 210 may execute computer instructions (program code) and, when executing the instructions, cause the processing device 120 to perform functions of the processing device 120 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the imaging device 110, the terminal(s) 130, the storage device 150, and/or any other component of the medical image acquisition system 100. For example, the processor 210 may obtain a plurality of medical images from the storage device 150, and determine a degree to which an artifact in the medical image affects recognition of a tissue feature. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the imaging device 110, the terminal(s) 130, the storage device 150, or any other component of the medical image acquisition system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program (e.g., in the form of computer-executable instructions) for the processing device 120 to extract a feature of the medial image. As another example, the storage 220 may store a program (e.g., in the form of computer-executable instructions) for the processing device 120 to determine the degree to which the artifact in the medical image affects recognition of the tissue feature.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 140) to facilitate data communications. The communication port 240 may establish connections between the processing device 120 and the imaging device 110, the terminal(s) 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating hardware and/or software components of a mobile device 300 according to some embodiments of the present disclosure. In some embodiments, the processing device 120 and/or the terminal(s) 130 may be implemented on the mobile device 300. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to the medical image acquisition system 100 from the processing device 120. User interactions with the information stream may be achieved via the I/O 350 and provided to the processing device 120 and/or other components of the medical image acquisition system 100 via the network 140.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate a high-quality image of a subject as described herein. A computer with user interface elements may be used to implement a personal computer (PC) or another type of work station or terminal device, although a computer may also act as a server if appropriately programmed. It is believed that those skilled in the art are familiar with the structure, programming, and general operation of such computer equipment and as a result, the drawings should be self-explanatory.

Figure 4:
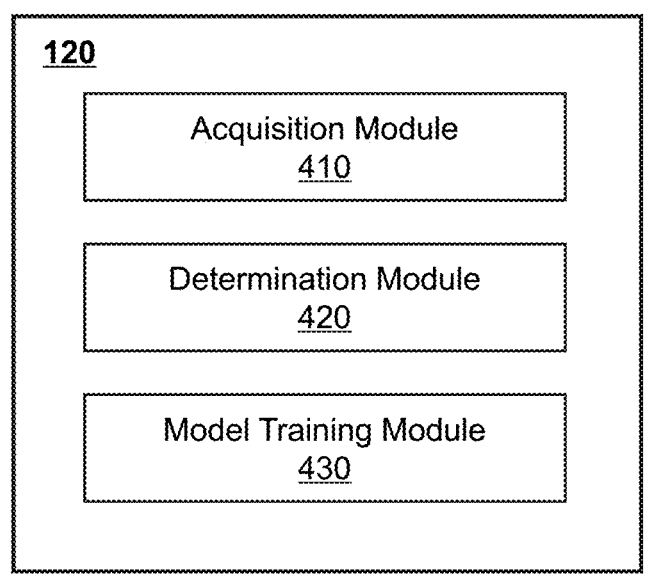
FIG. 4 is a schematic block diagram illustrating an exemplary processing device according to some embodiments of the present disclosure.

FIG. 4 is a schematic block diagram illustrating an exemplary processing device 120 according to some embodiments of the present disclosure.

The processing device 120 may include an acquisition module 410, a determination module 420, and a model training module 430.

The acquisition module 410 may be configured to acquire a medical image of a target object. The medical image refers to an image of internal tissues of the target object obtained in a non-invasive manner for clinical or medical research. In some embodiments, the target object may include a human body, an organ, a body, an object, an injury site, a tumor, or the like. In some embodiments, the acquisition module 410 may be configured to a plurality of sample medical images, and a label of each of the plurality of sample medical images. The label may represent a degree to which an artifact in each of the plurality of sample medical images affects the tissue feature recognition. The plurality of sample medical images and the label of each of the plurality of sample medical images may be used to train a preliminary determination model to generate a determination model. More descriptions regarding the acquiring of the medial image may be found elsewhere in the present disclosure. See, e.g., operations 510 and/or 710 and the relevant descriptions thereof.

The determination module 420 may be configured to determine information associated with the medial image. For example, the determination module 420 may extract a feature of each of the plurality of medical images (e.g., the acquired medical image, the sample medical images, etc.). The feature of each of the plurality of medical images may include a HOG feature of each of the plurality of medical images. As another example, the determination module 420 may determine a degree to which the artifact in the medical image affects recognition of the tissue feature by inputting the feature of the medical image to a determination model.

The model training module 430 may be configured to generate the determination model by training a preliminary determination model based on the extracted feature and the label of each of the plurality of medical images (e.g., the sample medical images). More descriptions regarding the generating of the determination model may be found elsewhere in the present disclosure. See, e.g., FIG. 7 and the relevant descriptions thereof.

The modules in the processing device 120 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units. For example, the determination module 420 and the model training module 430 may be combined as a single module configured to both determine the information of the medical image(s) and generate the determination model. As another example, the obtaining module 510 may be divided into two units. One of the two units may be configured to obtain the medical image of the target object, and the other one of the two units may be configured to obtain the sample medical images for training the determination model.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may further include a storage module (not shown in FIG. 4). The storage module may be configured to store data generated during any process performed by any component of the processing device 120. As another example, each of the components of the processing device 120 may include a storage device.

Additionally or alternatively, the components of the processing device 120 may share a common storage device.

Figure 5:
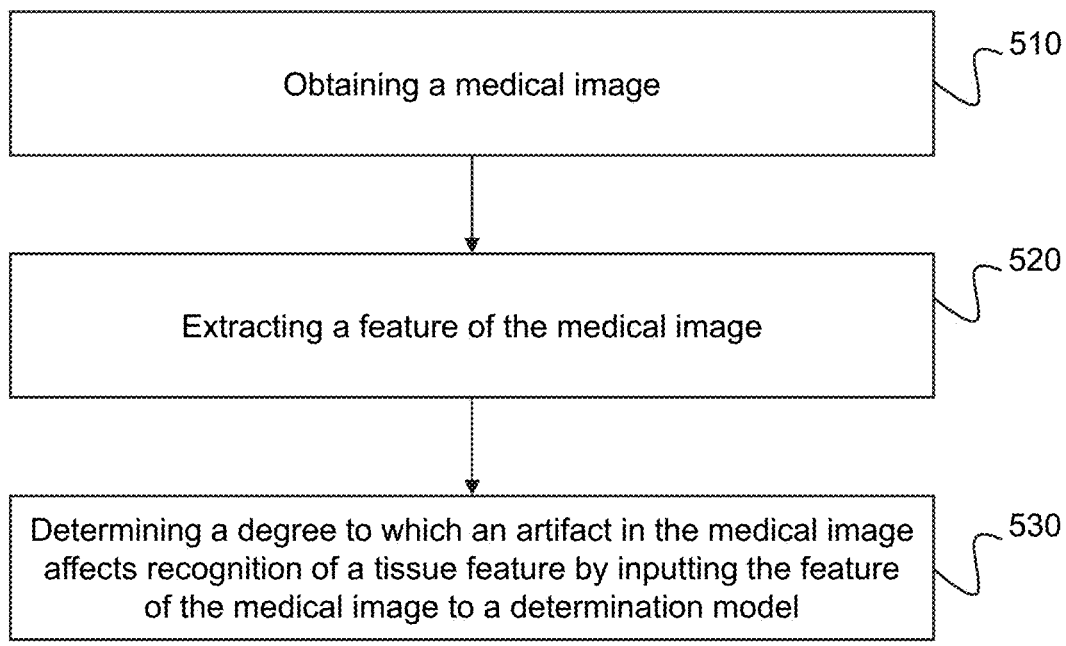
FIG. 5 is a flowchart illustrating an exemplary process for evaluating a medical image according to some embodiments of the present disclosure.

FIG. 5 is a flowchart illustrating an exemplary process 500 for evaluating a medical image according to some embodiments of the present disclosure.

In 510, the processing device 120 (e.g., the acquisition module 410) may acquire the medical image.

Figure 10A:
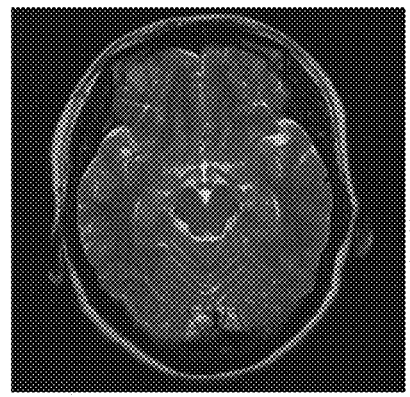
FIGS. 10A and 10B are schematic diagrams illustrating exemplary medical images according to some embodiments of the present disclosure.
Figure 10B:
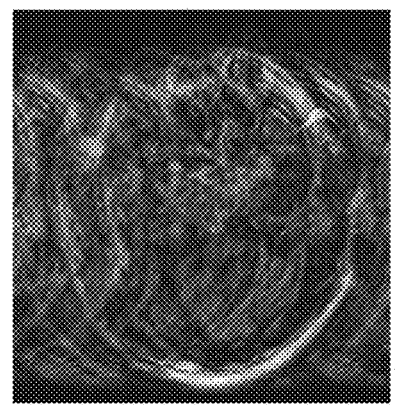

A medical image refers to an image of external or internal tissues of a target object obtained with an imaging technique for the purpose of research, diagnosis, prognosis, and/or treatment determination. In some embodiments, the medical image is obtained in a non-invasive manner. In some embodiments, the target object may include all or part of a human body, all or part of an organ, all or part of an animal body, all or part of a non-biological object, all or part of an injury/lesion site, all or part of a tumor, or the like. For example, the target object may include one or more lesions in the brain of a user. As shown in FIGS. 10A and 10B, a boundary and contrast between tissues and a background exists in the medical image 1000.

In some embodiments, the medical image may include, but is not limited to, an X-ray image, a computer tomography (CT) image, a positron emission tomography (PET) image, a single-photon emission computer tomography (SPECT) image, a magnetic resonance imaging (MRI) image, an ultrasound scan (US) image, a color doppler blood flow imaging (CDFI) image, a digital subtraction cardiovascular angiography (DSA) image, a magnetic resonance angiography (MRA) image, a time-of-flight magnetic resonance image (TOF-MRI), or a magnetoencephalography (MEG) image.

In some embodiments, the medical image may include a 2D image, a three-dimensional (3D) image, etc. In some embodiments, the 3D image may include a series of 2D slices or layers.

In some embodiments, a format of the medical image may include a Joint Photographic Experts Group (JPEG) image format, a Tagged Image File Format (TIFF) image format, a Graphics Interchange Format (GIF) image format, a Kodak Flash PiX (FPX) image format, a Digital Imaging image format, and a Communications in Medicine (DICOM) image format.

The medical image may include an artifact. An artifact refers to a portion of an image that does not correspond to any part that actually exists in the target object. For example, the artifact may include image distortion, image overlap, image loss, image blur, or the like, or any combination thereof. The artifact may include different types according to its causes, for example, a patient-related artifact, a signal-related artifact, or the like, or any combination thereof. The patient-related artifact may include a motion artifact, a laminar flow artifact, a metal artifact, or the like. The signal-related artifact may include a chemical shift artifact, a partial volume artifact, an aliasing artifact, or the like, or any combination thereof.

Different artifacts in different types may have different features. For example, the metal artifact may be caused by magnetic field deformation that is caused by a ferromagnetic substance carried by a user during image acquisition. The metal artifact may cause deformation or distortion of the medical image. As another example, the motion artifact may be caused by a macroscopic motion of a tissue in the target object. As shown in FIGS. 10A and 10B, FIG. 10A illustrates a medical image that does not include a motion artifact, and FIG. 10B illustrates a medical image that includes a motion artifact. The motion artifact may be represented by the superimposed appearance of tissues and low-density shadows. Because of a morphological feature of the motion artifact, a texture feature of the motion artifact may be obvious.

The artifact generally reduces the imaging quality of the medical image, and further affects the perception and/or analysis (e.g., diagnosis) of the target object. For example, the metal artifact may affect the determination of a shape and/or position of the target object. As another example, the faster the frequency and the larger amplitude of the motion, the more the images overlap and the more obvious the motion artifacts are, which may seriously affect the analysis of the medical image.

In some embodiments, the processing device 120 may obtain the medical image from one or more components of the medical image acquisition system 100 in a wired or wireless manner. For example, the processing device 120 may acquire the medical image from the imaging device 110. As another example, the processing device 120 may acquire the medical image from the storage device 150 in the medical image acquisition system 100. In some embodiments, the processing device 120 may acquire the medical image from external of the medical image acquisition system 100, for example, an external storage device.

In some embodiments, the processing device 120 may acquire the medical image through an interface. The interface may include a program interface, a data interface, a transmission interface, or the like. For example, the medical image acquisition system 100 may be called by an external device or a system, and the medical image may be transmitted to the medical image acquisition system 100.

The medical image may have different transmission speeds and time-consuming in different acquisition modes. In some embodiments, the processing device 120 may select an acquisition mode according to different application scenarios. For example, if the medical image is evaluated in real time during a process of acquiring the medical image, the processing device 120 may obtain the medical image by selecting a fastest mode to save the entire evaluation time, and at the same time, the imaging device 110 may quickly re-acquire the medical image to reduce equipment wear and save patient's time.

In some embodiments, the processing device 120 may preprocess the acquired medical image. In some embodiments, the preprocessing of the medical image may include regularizing a size of the medical image to exclude an impact of the size on an evaluation of the medical image. For example, the processing device 120 may perform a regularization by scaling and/or cropping the medical image to a same size and not changing a proportional relationship of the medical image. In some embodiments, the regularization of the medical image may include a Tikhonov regularization, a total variation regularization, a gradient L0 regularization, or the like.

In some embodiments, the preprocessing of the medical image may further include normalizing color(s) of the medical image. In some embodiments, the color normalization may include a graying, a gamma correction (also known as a power law transformation), or the like.

In some embodiments, a graying refers to a process of changing an image containing brightness and color(s) into a grayscale image. Color(s) of an image can be represented by an RGB model. The RGB model may assign an intensity value in the range of 0 to 255 to each of RGB components of each pixel of the image. The RGB components may include a red (R) component, a green (G) component, and a blue (B) component. After the graying, the values of the RGB components of the image may be the same. The value may be referred to as a gray value after graying. The gray value may be a real number between 0 and 255, which may represent one of 256 gray levels between the white and the black.

In some embodiments, the graying may include, but is not limited to, a component graying, a maximum graying, an average graying, a weighted average graying, or the like. For example, the averaging graying may average the values of the three RGB components, and the obtained average value may be assigned as the gray value. It can be understood that the graying may reduce the color types of the medical image, thereby reducing the amount of data processing in the process of extracting a feature of the medical image, and improving the efficiency of the data processing.

In some embodiments, the gamma correction may adjust the contrast of the medical image, thereby reducing the impact of local shadows and changes in image brightness, while suppressing noise interference. Specifically, the gamma correction may perform an exponential transformation on the gray value of the input medical image, so that the brightness deviation between a highlight portion and a darkening portion may be increased, thereby improving the contrast effect of the medical image. In some embodiments, the gray value of the noise may be high and the gray value of the tissue may be low. The darkening portion can be expanded and the highlight portion may be compressed based on the gamma correction, thereby distinguishing the noise and the tissue and reducing noise interference.

In some embodiments, the preprocessing may further include other processes, and the present disclosure is not intended to be limiting. For example, the preprocessing may also include a geometric transformation, an image enhancement, an image smoothing, or the like.

In 520, the processing device 120 (e.g., the determination module 420) may extract a feature of the medical image. In some embodiments, the feature of the medical image may include a directional histogram (HOG) feature of the medical image.

A feature of a medical image refers to a feature for evaluating the quality of the medical image. In some embodiments, the feature of the medical image may include a microscopic feature. For a planar image, the microscopic feature may include a pixel-level feature, a sub-pixel-level feature, or the like. For a stereo image, the microscopic feature may include a feature in a stereo pixel level. In some embodiments, a type of the microscopic feature may include an edge feature, a texture feature, a color feature, a shape feature, and the like.

In some embodiments, the microscopic feature of the medical image may be obtained in a plurality of ways. For example, the microscopic feature may be obtained through an algorithm. An extraction algorithm of the microscopic feature may include, but is not limited to, a HOG algorithm, a local binary pattern (LBP) algorithm, and a scale-invariant feature scale matching algorithm, a Scale Invariant Feature Transform (SIFT) algorithm, a Haar-like algorithm, a Gray-level co-occurrence matrix (GLCM), a structured algorithm, an energy spectrum function algorithm, a Hough transform algorithm, a Fourier transform algorithm, etc.

HOG refers to a feature description used in a computer vision and an image processing for object detection. The feature of the medical image may be formed by calculating and counting the HOG of local regions of a medical image. The HOG algorithm may characterize a shape feature and texture feature of the medical image based on a directional density distribution of an image edge or the brightness gradient of the medical image. As mentioned above, a boundary and contrast between the background and the target object may exist in the medical image. The texture feature of the artifact may be obvious. Therefore, the HOG algorithm may be used to extract the microscopic feature of the medical image.

In some embodiments, the processing device 120 may extract the HOG feature of the medical image based on the HOG algorithm, and the HOG feature of the medical image may be represented by a multi-dimensional vector. More descriptions regarding the extraction of the HOG feature may refer to FIG. 6 and related descriptions, and not repeated herein.

In some embodiments, the feature of the medical image may also include a macroscopic feature. A macroscopic feature refers to a scanned feature in the medical image. The macroscopic feature may include but not limited to a tissue type contained in the medical image, a gender of a user to which the medical image belongs, the age of the user, etc.

The gender of the user to which the medical image belongs refers to the gender of the user to which a target object of the medical image belongs. The age of the user to which the medical image belongs refers to the age of the user to which the target object of the medical image belongs.

A tissue type of the medical image refers to the tissue type of the target object scanned by an imaging device. It is understood that the tissue may be a tissue in a human and/or an animal. In some embodiments, the tissue type may include a human or an animal site type, such as a lung, a liver, a spleen, blood vessels, etc. The tissue type may also be determined by cell composition, such as an epithelial tissue, a connective tissue, a muscle tissue, a nerve tissue, etc.

In some embodiments, the macroscopic feature may be read directly from internal of the medical image acquisition system 100 (e.g., the imaging device 110, the storage device 150, the terminal 130) or external of the medical image acquisition system 100. For example, when the target object is diagnosed, the tissue type of the target object and a file (e.g., age, gender, or medical historical record) of the target object may be inputted via the terminal 130.

In some embodiments, the processing device 120 may extract a feature of the artifact and further determine whether the artifact affects recognition of a tissue feature based on the feature of the artifact. For example, before extracting the feature of the medical image, the processing device 120 may identify the artifact in the medical image and extract the feature of the artifact.

In some embodiments, the processing device 120 may identify the artifact in the medical image through a neural network model. For example, the processing device 120 may divide the medical image into a plurality of blocks based on an anatomy and/or a position, and then input each of the blocks into the neural network model for artifact recognition to obtain one or more probability values. Based on the probability values and a preset threshold, the processing device 120 may determine whether each of the blocks has the artifact. In some embodiments, the neural network model may include but is not limited to, a Visual Geometry Group (VGG) Network model, an Inception NET model, a Fully Convolutional Networks (FCN) model, a Segmentation Network (SegNet) model, a DeepLab model, a Mask-RCNN (a Mask-Region Convolutional Neural Networks or a Mask-Convolutional Neural Network) model, etc.

In 530, the processing device 120 (e.g., the determination module 420) may determine a degree to which the artifact in the medical image affects recognition of the tissue feature by inputting the feature of the medical image to a determination model.

The determination model may determine whether the artifact in the medical image affects recognition of the tissue feature, or the degree that the artifact affects the recognition of the tissue feature based on the inputted feature. It can be understood that the more serious the artifact is, the worse the quality of the medical image is, the deeper the effect of the artifact to the recognition of tissue feature is. Therefore, there may be a corresponding relationship between the quality of the medical image and the degree to which the artifact in the medical image affects recognition of the tissue feature.

In some embodiments, the recognition of tissue feature may include that a doctor or a medical device identifies each feature of the tissue type in the medical image. The feature may include a shape of the tissue, an outline of the tissue, a brightness of the tissue, or a degree of shadows of the tissue. Further, the doctor or medical device may diagnose or analyze the target object according to the identified tissue feature.

In some embodiments, the processing device 120 may process the feature of the medical image before inputting the feature of the medical image into the determination model. For example, the processing may include Nesterov, transforming the feature to categorical data, or/and data crossing.

In some embodiments, the determination model may obtain a corresponding value or probability based on the feature of the medical image, and then determine the degree to which the artifact in the medical image affects recognition of the tissue feature. In some embodiments, the value or probability may be compared with a threshold to obtain a determination and/or evaluation result.

In some embodiments, the degree to which the artifact in the medical image affects recognition of the tissue feature may be determined according to actual needs. For example, the degree to which the artifact in the medical image affects recognition of the tissue feature may include "effective" and "no effective". As another example, the degree to which the artifact in the medical image affects recognition of the tissue feature may include "serious effective", "minor effective", "no effective", etc. The degree to which the artifact in the medical image affects recognition of the tissue feature may also be in any other way, and the present disclosure may not limit thereto.

In some embodiments, the feature inputted into the determination model may include one feature type or any combination of feature types. More descriptions regarding the various feature types may be found in 520, which will not be repeated herein.

In some embodiments, the feature inputted into the determination model may include the microscopic feature of the medical image, for example, the HOG feature of the medical image. In medical image(s), the microscopic features of medical image(s) of different tissue types may be different. For example, a medical image of the skull may have fewer texture features, and a medical image of an abdominal cavity may have more texture features. The texture features of a medical image with artifact may be multiple times of the texture features of a medical image without an artifact. A direction feature of the texture in the medical image may be used to characterize different portions corresponding to the medical image to a certain extent. In this case, a determination model may be used to evaluate medical images corresponding to different portions.

In order to further improve determination accuracy, in some embodiments, the feature inputted into the determination model may also include the macroscopic feature, for example, a type of tissue, the age of the user, or the like. The macroscopic feature may be represented by a numeric value, for example, "1" represents the brain, "2" represents the heart, and "3" represents the lungs. In some embodiments, the processing device 120 may convert the numerical value representing the macroscopic feature into a vector using the bucketing.

The processing device 120 may input the HOG feature and the tissue type into the determination model. The determination model may determine differentiated determination results for different tissue types, which can improve the accuracy of the evaluation of the determination model.

In some embodiments, the determination model may include a shallow learning model, a deep learning model, or the like. The shallow learning model may include, but is not limited to, a support vector machine (SVM) model, a Logistic Regression model, a Naive Bayes classification model, a decision tree model, or the like.

The SVM model may be a linear binary classifier that can obtain a determination result based on a positional relationship between the feature of medical image and a decision boundary. For example, the decision boundary may include two sides. One side of the two sides may represent the "effective", and another side of the two sides may represent the "no effective". When the feature of the medical image is on the "effective" side of the decision boundary, the determination result may be "effective". The decision boundary refers to a maximum margin hyperplane obtained by an SVM based on training samples and learned through a kernel function. In some embodiments, the kernel function may include but not limited to, a linear kernel function, a polynomial kernel function, a Gaussian (RBF) kernel function, a sigmoid3 kernel function, etc.

The deep learning model may include a neural network model. The neural network model may map the feature of the medical image to a value or probability based on parameters of each layer of the network, and then obtain a determination result based on the value or probability. In some embodiments, the neural network model may include, but is not limited to, a Deep Neural Network (DNN), a Convolutional Neural Network (CNN) model, and a Recurrent Neural Network (RNN) model.

In some embodiments, the determination model may be selected according to different application scenarios. The higher the accuracy requirement of the scenario for the determination is, the more layers of the determination model may be used. For example, the deep learning model may be selected. In this scenario, after the scan, a doctor may diagnose and draw a conclusion based on the scanned medical image. In scenarios with time and speed requirements, the shallow learning model may be selected, which may be an evaluation of a medical image during a scan to determine if a rescan is needed.

In some embodiments, a type of the determination model may be determined based on the feature type. For example, the deep learning model may be selected for a complicated inputted feature, that is the determination model may need to learn more features. Merely by way of example, the inputted feature may include the macroscopic feature and the microscopic feature, the deep neural network may be selected.

In some embodiments, the type of the determination model may be selected according to the amount of training data. The feature used in deep learning may be extracted by a deep learning model. Preliminarily, the deep learning model may not obtain a determination result. The deep learning model may continuously extract the features and adjust a weight of each of the extracted features. The deep learning model may determine the feature(s) and a weight of each of the feature(s) for determining the determination result. In this way, the deep learning model may need multiple training data to obtain the determination result. Thus, the deep learning model may be difficult to apply to scenarios with less training data, and the preparation of training data may cost time.

In some embodiments, different tissues may correspond to different determination models. The tissues with the same tissue type may correspond to an identical determination model. For example, different lungs may correspond to an identical determination model, different hearts may correspond to another determination, or the like. When a medical image is obtained, a determination model corresponding to the tissue type image may be determined according to the tissue type of the tissue to which the medical image belongs, and further, the feature of the medical image may be inputted into the determined determination model to obtain a determination result.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 6:
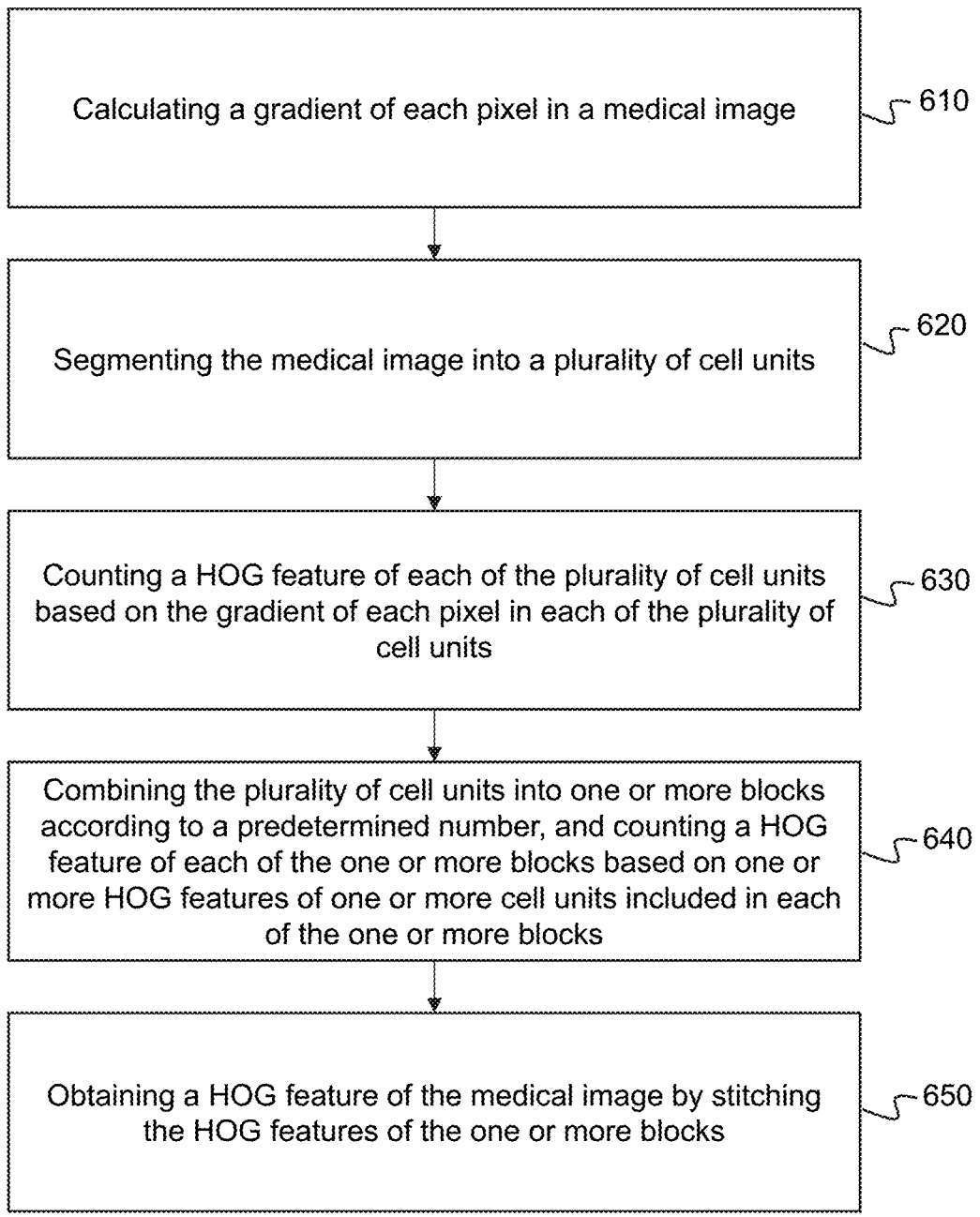
FIG. 6 is a flowchart illustrating an exemplary process for extracting a HOG feature of a medical image according to some embodiments of the present disclosure.

FIG. 6 is a flowchart illustrating an exemplary process for extracting a HOG feature of a medical image according to some embodiments of the present disclosure.

In 610, the processing device 120 (e.g., the determination module 420) may determine a gradient of each pixel in the medical image.

A pixel refers to the finest distinguishable element in an image. An image may be actually a function, and in some embodiments, the image may be represented by a 2D discrete function. The gradient of each pixel refers to a derivative of a 2D discrete function representing an image at a pixel, which may represent a rate of change of a pixel value. In some embodiments, the pixel value may represent a gray value or an RGB value at a corresponding position of the pixel in the image.

The gradient of each pixel may include a magnitude and a direction of the gradient. The gradient of each pixel can reduce interference of light, and contour information of the tissue in the image may be extracted. In some embodiments, the gradient of each pixel may be determined based on the gradient of the pixel in different directions. The direction may be determined through customization, or any direction in a 2D coordinate system, for example, a plane rectangular coordinate system, a polar coordinate system, or the like.

Taking the plane rectangular coordinate system as an example, a gradient of a pixel may be determined based on a horizontal gradient and a vertical gradient of the pixel, which may refer to equations (1) and (2):

$$G(x, y) = \sqrt{G_h(x, y)^2 + G_v(x, y)^2}, \quad (1)$$

$$\alpha(x, y) = \arctan\left(\frac{G_v(x, y)}{G_h(x, y)}\right), \quad (2)$$

wherein G(x, y) represents the gradient, α(x, y) represents a gradient direction, $G_h$(x, y) represents the horizontal gradient of the pixel, and $G_v$(x, y) represents the vertical gradient of the pixel.

In some embodiments, the gradient direction may be 0~180 degrees or 0~360 degrees. When the gradient direction is from 0 to 180 degrees, the gradient of each pixel may include an unsigned gradient (see equation (3)). When the gradient direction is 0~360 degrees, the gradient of each pixel may include a signed gradient.

$$(x, y) = \begin{cases} \alpha(x, y) + \pi, \alpha(x, y) < 0 \\ \alpha(x, y), \alpha(x, y) \geq 0 \end{cases}, \quad (3)$$

In some embodiments, the gradients of the medical image in different directions may be determined based on one or more manners. For example, the medical image may be filtered through a kernel to obtain the gradients of the medical image in different directions. As another example, a one-dimensional discrete differential template may be used to process the medical image in one direction, and the gradients of the medical image in different directions may be obtained. As another example, an extraction operator (e.g., a Prewitt operator, a Sobel operator, a Laplacian operator, etc.) may be used to obtain the gradients of the medical image in different directions.

In 620, the processing device 120 (e.g., the determination module 420) may segment the medical image into a plurality of cell units, wherein each of the plurality of cell units may include a same count of pixels.

A cell unit refers to a unit grid by segmenting the medical image. In some embodiments, each of the cell units may include the same number or count of pixels. For example, each of the cell units may include 64 pixels.

Figure 9:
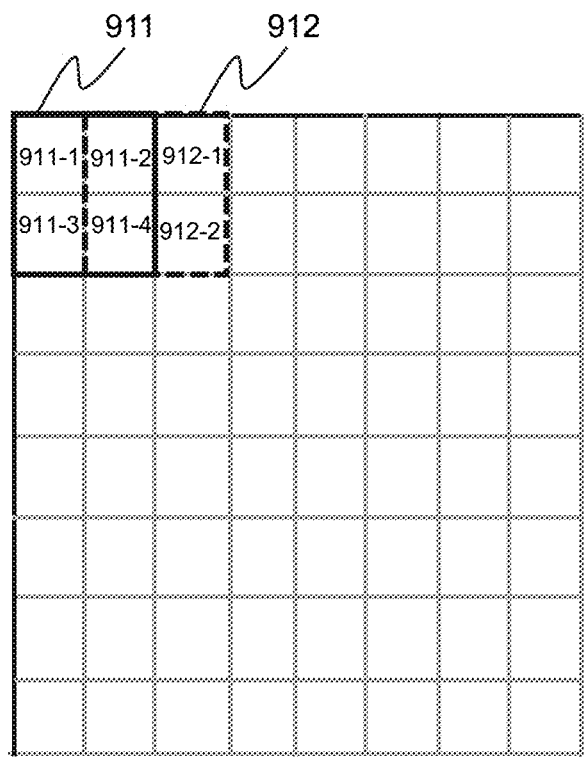
FIG. 9 is a schematic diagram illustrating exemplary blocks of a medical image according to some embodiments of the present disclosure.

In some embodiments, the cell units may be rectangular. As shown in FIG. 9, the medical image 900 may include 64×64 pixels. If each of the rectangle cell units includes 8×8 pixels, the medical image 900 of 64×64 pixels may be segmented into 8×8 cell units. In some embodiments, the cell units may also be astroid. For example, each of the cell units may include 64 pixels, and a medical image with 12288 pixels may be segmented into 192 astroid unit cells.

In 630, the processing device 120 (e.g., the determination module 420) may count a HOG feature of each of the plurality of cell units based on the gradient of each pixel in each of the plurality of cell units In some embodiments, the processing device 120 may obtain the HOG feature of each of the cell units based on a distribution density of the gradient of each pixel of each of the cell units in the gradient direction. It should be understood that each of cell units may correspond to a HOG feature.

In some embodiments, the HOG feature of each of the cell units may be obtained according to the following process. For example, the processing device 120 may divide the gradient direction into a plurality of ranges, count a gradient corresponding to the pixels distributed in each range of the gradient direction, and determine the HOG features of the cell units based on the counted gradient.

In some embodiments, the gradient direction may be divided into a plurality of same ranges. For example, the gradient direction from 0 to 180 degrees may be divided into 9 ranges including 0 to 20 degrees, 20 to 40 degrees, 40 to 60 degrees, 60 to 80 degrees, 80 to 10 degrees, 100 to 120 degrees, 120 to 140 degrees, 140 to 160 degrees, and 160 to 180 degrees. Each range may be referred to as a bin.

In some embodiments, a value of each bin may be determined based on the gradient of each pixel included in the bin. For example, if a bin of 0 to 20 degrees includes a pixel A with a gradient of 3, a pixel B with a gradient of 2, a pixel C with a gradient of 4, and a value of the bin of 0 to 20 degrees is a sum of gradients of the pixel A, B, and C, that is 9.

In some embodiments, the pixels in a bin may be determined based on the gradient direction of each pixel and the range of the bin. For example, if the gradient direction of the pixel A is 12 degrees, the pixel A belongs to a bin of 0 to 20 degrees. If the gradient direction of the pixel D is 133 degrees, the pixel D belongs to a bin of 120 to 140 degrees.

In some embodiments, the value of each bin may be used as an element of a HOG feature vector of each cell unit. Merely by way of example, if the gradient direction may be divided into 9 ranges, and the values of the 9 bins corresponding to cell units X are 9, 50, 100, 120, 130, 150, 90, 60, and 30, respectively, the HOG feature of the cell units X may be represented as a 9-dimensional vector [9,50,100, 120,130,150,90,60,30].

In 640, the processing device 120 (e.g., the determination module 420) may combine the plurality of cell units into one or more blocks according to a predetermined number, and count a HOG feature of each of the one or more blocks based on one or more HOG features of one or more cell units included in each of the one or more blocks.

The processing device 120 may segment the medical image into larger units based on the blocks, and extract corresponding block HOG features based on the larger units.

In some embodiments, a block may be a rectangular block including a plurality of cell units. Specifically, a fixed-size rectangle block may be slid in the medical image based on a step size, and the medical image may be divided into a plurality of rectangle blocks with a same size.

In some embodiments, the step size may be less than the size of the rectangle block, and accordingly, cell units in a rectangle block may coincide with cell units in another rectangle block. In some embodiments, the step size may be a cell unit. As shown in FIG. 9, the medical image 900 includes 64×64 pixels, and each cell unit includes 8×8 pixels. If each block includes 2×2 cell units, and a step size is a cell unit, the medical image includes 49 (i.e., 7×7) blocks. As seen from FIG. 9, cell units 911-2, 911-4 included in block 912 may coincide with the cell units of the rectangle block 911.

In some embodiments, the step size may be equal to the size of the rectangle block, and accordingly, the rectangle blocks may be closely adjacent to each other. In some embodiments, the step size may be larger than the size of the rectangle block, and accordingly, a space may be formed between cell units included in each rectangle block.

In some embodiments, the block may also be a circular block including a plurality of cell units. For example, the aforementioned medical image may be divided into 192 astroid cell units, and 16 astroid cell units may form a circle block, thereby dividing the medical image into 12 circle blocks.

In some embodiments, one or a combination of the rectangular block and the circular block may be selected based on the tissue type. For example, to avoid segmenting the eyes in a medical image, the processing device 120 may select a circular block to extract a feature.

It should be understood that a rectangular HOG (R-HOG) feature or a circular HOG (C-HOG) feature may be obtained based on the HOG feature of each cell unit in the rectangular block or the circular block.

In some embodiments, the HOG feature of each block may be obtained based on the HOG feature of each of the cell units. For example, the HOG feature of each of the cell units included in a block may be stitched, and the stitched feature may be used as the HOG feature of the block. Specifically, if a rectangular block may include 2×2 rectangular cell units, and each rectangular cell unit is a 9-dimensional vector, a vector of a HOG feature of each rectangle block may be a (2×2×9)-dimensional vector.

In some embodiments, in order to unify the order of data and improve the efficiency and effectiveness of subsequent algorithms, the processing device 120 may normalize the HOG feature of each block. In some embodiments, the normalization may include but is not limited to an $L_2$-norm, an $L_2$-hys, an $L_1$-norm, an $L_1$-sqrt, or the like, or any combination thereof.

In 350, the processing device 120 (e.g., the determination module 420) may obtain a HOG feature of the medical image by stitching the HOG features of the one or more blocks.

In some embodiments, the HOG features of the blocks may be directly stitched to obtain the feature of the medical image. Continuing with the foregoing example, a 64×64 medical image may include 7×7 blocks, and a vector dimension of the HOG feature of the medical image is 7×7× (2×2×9).

In some embodiments, the HOG features of the plurality of blocks may be stitched based on a weight corresponding to each of the blocks to obtain the feature of the medical image. In some embodiments, the weight may be determined based on a position of each of the blocks in the medical image. For example, a rectangle block of a target object may have a relatively large weight and a rectangle block of a background may have a relatively small weight.

In some embodiments, if the medical image is a color image and is not grayed, HOG features of a plurality of sets of color components may be obtained based on the color components. The HOG feature of the medical image may be determined based on the HOG features of the plurality of sets of color components. For example, pixel values of three color components may be obtained based on a red (R), a green (G), and a blue (B) components of the RGB color. Based on the pixel values of each color component, a HOG feature of each of the three color components may be obtained as shown in FIG. 6. The HOG feature of the medical image may be obtained based on the HOG features of the red (R), green (G), and blue (B) components.

In some embodiments, a technique for obtaining the HOG feature of the medical image based on the HOG features of the plurality of sets of color components may include, but is not limited to, a component technique, a maximum technique, an average technique, a weighted average technique, or the like. For example, an average value of the HOG features of the red (R) color component, the green (G) color component, and the blue (B) color component may be regarded as the HOG feature of the medical image.

In some embodiments, a feature of a 3D medical image may be acquired based on features of a plurality of 2D medical images. Specifically, the processing device 120 may convert a 3D medical image into N 2D layers or slices based on N directions. The processing device 120 may determine a feature of each of the 2D layers. The processing device 120 may determine the feature of the 3D medical image using the maximum technique, the average technique, the weighted average technique, or other techniques based on the feature of each of the N 2D layers. For example, a 3D medical image may be converted into three 2D layers in three directions of X, Y, and Z, and a feature X of a medical image, a feature Y of the medical image, and a feature Z of the medical image may be obtained. The maximum feature X of the medical image may be used as the final feature of the medical image for further processing.

Figure 7:
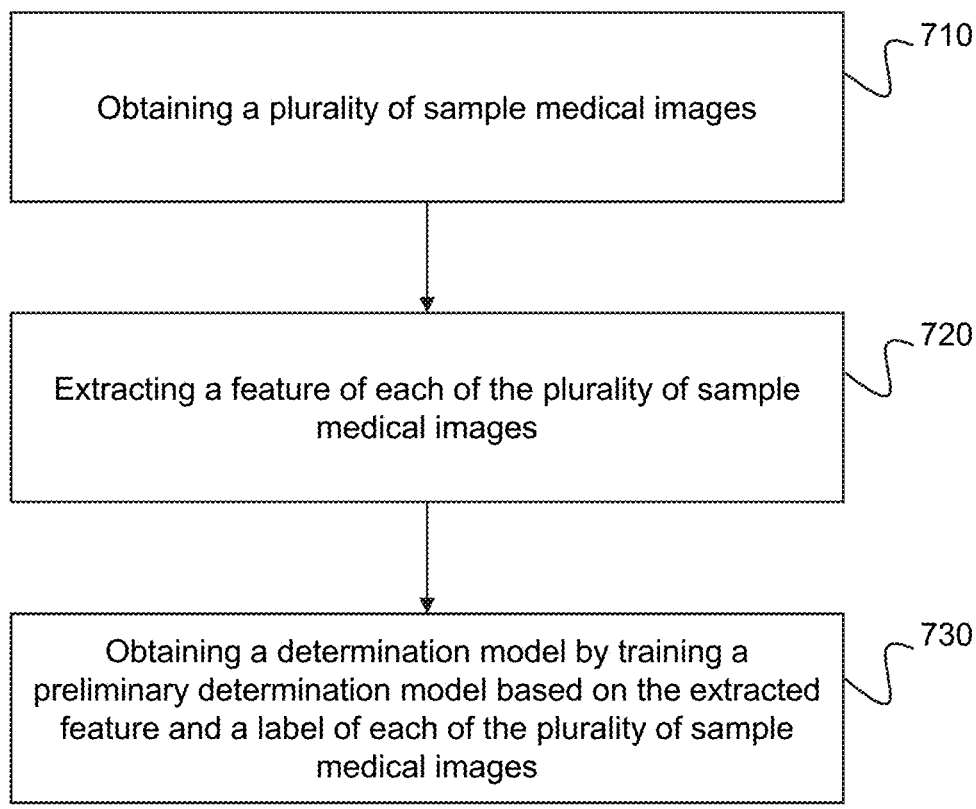
FIG. 7 is a flowchart illustrating an exemplary process for determining a determination model according to some embodiments of the present disclosure.

FIG. 7 is a flowchart illustrating an exemplary process for obtaining a determination model according to some embodiments of the present specification.

In 710, the processing device 120 (e.g., the acquisition module 410) may acquire a plurality of sample medical images, and a label of each of the plurality of sample medical images. The label may represent a degree to which an artifact in each of the plurality of sample medical images affects the tissue feature recognition.

In some embodiments, the processing device 120 may obtain a sample medical image set from a storage device internal or external of the medical image acquisition system 100. The sample medical image set may include the plurality of sample medical images and the label of each of the sample medical images. The label of each of the sample medical images may be determined by manual annotation or other modes, which are not limited in the present disclosure.

As mentioned above, the determination model may determine that the medical image may have two types The two types of the medical image may include "no effective" and "effective", and the label of the sample medical images may be the two types. A label of a sample medical image which may have no artifact or the artifact may not affect recognition of the tissue feature may be "no effective", and a label of a sample medical image which may have the artifact and the artifact may affect the recognition of the tissue feature may be "effective". The determination model may determine that the medical image may have three types. The three types of the medical image may include "serious", "medium", and "minor". A label of a sample medical image where the artifact seriously affects the recognition of the tissue feature may be annotated as "serious". A label of a sample medical image where the artifact moderately affects the recognition of the tissue feature may be annotated as "medium". A label of a sample medical image where the artifact slightly affects the recognition of the tissue feature may be annotated as "minor". In some embodiments, the label of the sample medical image may be represented by a numerical value. The sample medical image and the label of the sample medical image may also be represented by other forms, which are not limited in the present disclosure.

In some embodiments, the sample medical images of the sample medical image set may include preprocessed medical images, thereby excluding the influence of a size, a color, a brightness, etc. of the medical image for training the determination model. More descriptions regarding the preprocessing of the medical image may be seen in FIG. 5 and will not be repeated herein.

In some embodiments, the plurality of sample medical images in the sample medical image set may be mirror-processed to obtain more medical images as a training set.

In some embodiments, a type of each of the sample medical images may be the same as the type of the medical image. The type of each of the sample medical images may include a tissue type, a device type, and a type of a user to which a target object belongs (e.g., an age, a gender, etc.). Using the sample medical images to train the determination model may improve the determination accuracy of the determination model. Preferably, a tissue type of each of the sample medical images may be the same as the tissue type of the medical image. For example, a medical image determined by the determination model is a medical image of a lung, and the sample medical images may include medical images of a lung.

In 720, the processing device 120 (e.g., the determination module 420) may extract a feature of each of the plurality of sample medical images.

As described in FIG. 5, the feature of the medical image may include the HOG feature of the medical image, the gender of the user to which the medical image belongs, the age of the user to which the medical image belongs, and/or the tissue type of the medical image. More descriptions regarding the feature extraction of the medical image may refer to FIG. 6 and the relevant descriptions, and not repeated herein.

In some embodiments, the training set may be extracted from the sample medical image set. The training set may include a plurality of training samples. A feature and a label of a sample medical image may constitute a training sample.

In some embodiments, the training samples in the training set may have positive and negative samples. A positive sample refers to a sample obtained from sample medical images where artifact(s) may not affect the recognition of the tissue feature, and a negative sample refers to a sample obtained from sample medical images where artifact may affect the recognition of the tissue feature. In some embodiments, a number/count of the negative samples in the training samples may be 2-3 times that of the positive samples, which may improve the determination accuracy of the determination model trained using the training samples.

In addition, a validation set may be extracted from the sample medical image set. The validation set may include a plurality of validation samples. A feature and a label of a sample medical image may constitute a validation sample. Preferably, the samples in the validation set and the samples in the training set may have no intersection, that is, the validation set and the training set may be not extracted from same sample medical images. After obtaining the validation set, a cross-validation technique may be used to verify a training level of the determination model to enhance a generalization ability of the determination model and avoid overfitting of the determination model.

In 730, the processing device 120 (e.g., the model training module 430) may obtain the determination model by training a preliminary determination model based on the extracted feature and the label of each of the plurality of sample medical images.

In some embodiments, the processing device 120 may determine the determination model based on the plurality of sample medical images using general manners. Specifically, the processing device 120 may input the feature and the label of each of the sample medical images into the preliminary determination model, and update parameters of the preliminary determination model by training the preliminary determination model until a preset condition is satisfied. The preliminary determination model with updated parameters may be designated as the determination model. The preset condition may include that a loss function may convergence, the loss function may be less than a preset threshold, a count of training cycles may be less than a count threshold, etc.

In some embodiments, a training algorithm may include, but is not limited to, a Gradient Descent algorithm, a Nesterov Accelerated Gradient algorithm, an Adaptive gradient (Adagrad) algorithm, and an adaptive learning rate algorithm (Adam), or the like.

As described in operation 510, the texture features of the medical images of different tissue types may be different. Therefore, different tissue types may correspond to different determination models. In this way, it is necessary to train a corresponding preliminary determination model for each of the tissue types to obtain a corresponding determination model. The corresponding determination model may be used to evaluate a medical image with such tissue type, thereby reducing the training time of each of the preliminary determination models and improving the determination accuracy of each of the determination models. Specifically, for a certain tissue type, a preliminary determination model corresponding to the tissue type may be trained based on sample medical images containing the tissue type, and a determination model corresponding to the tissue type may be obtained. For example, to obtain a determination model for a lung, the preliminary determination model may be trained with sample medical images that contains or only contains a lung.

After training the preliminary determination models corresponding to different tissue types to obtain the corresponding determination models, the processing device 120 may select a corresponding determination model based on a current scanned tissue type, and input acquired medical image(s) into the corresponding determination model to determine an evaluation result.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 8:
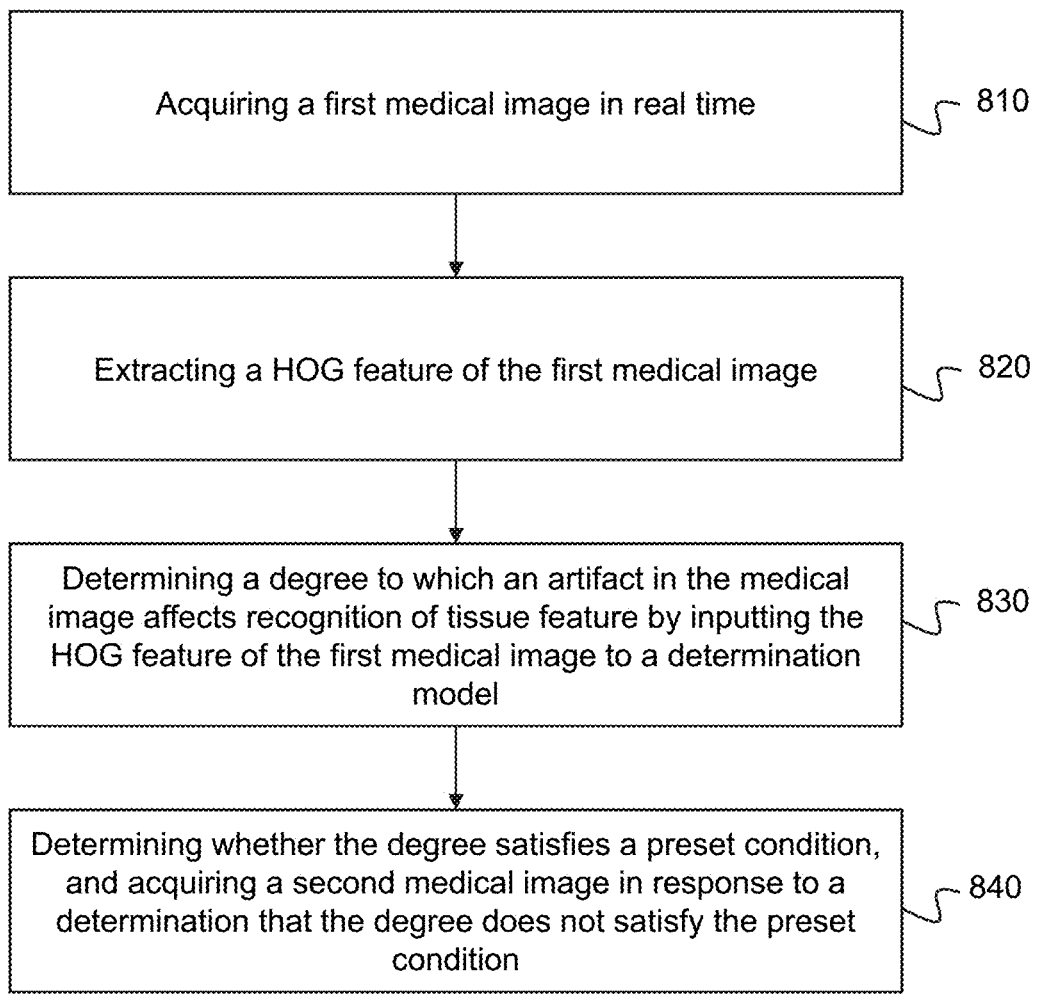
FIG. 8 is a flowchart illustrating an exemplary process for acquiring a medical image according to some embodiments of the present disclosure.

FIG. 8 is a flowchart illustrating an exemplary process for acquiring a medical image according to some embodiments of the present disclosure.

In some embodiments, an artifact in the medical image obtained by the medical image acquisition system 100 may seriously affect recognition of a tissue feature, a doctor cannot make a diagnosis based on the medical image, and another medical image of a target object may be reacquired. It is necessary to ensure the quality of all or a portion of the medical image during a scan of the target object. Therefore, during the scan, the quality of the medical image may be evaluated in real time. If the quality does not meet a need, for example, the artifact in the medical image seriously affects the recognition of the tissue feature, the processing device 120 may cause the medical image acquisition system 100 to perform a rescan until an acquired medical image meets the need.

In 810, the processing device 120 (e.g., the acquisition module 410) may reacquire a first medical image in real time.

A real-time acquisition refers to that the imaging device 110 may transmit the medical image to the processing device 120 through the network 140 while scanning the target object, so that the processing device 120 may evaluate the medical image in real time. Therefore, when the quality of the medical image is not high, for example, when the artifact of the medical image severely affects the degree of recognition of the tissue feature, the imaging device 110 may reacquire another medical image in time, thereby saving time and improving efficiency.

A first medical image refers to a medical image of the target object acquired by the imaging device 110 when the target object is on a current position. Detailed descriptions regarding the medical image may refer to FIG. 5 and the relevant descriptions thereof, and not repeated herein.

In 820, the processing device 120 (e.g., the determination module 420) may determine whether the degree to which the artifact in the medical image affects the recognition of the tissue feature satisfies a preset condition in real time.

The preset condition may be determined according to a diagnosis, for example, medical images with high quality may be needed for the diagnosis. The preset condition may be determined as that the degree of the artifact affecting recognition of the tissue feature is "no effective" or "minor".

After the first medical image is acquired, the processing device 120 may input the first medical image to a determination model for determining or evaluating the degree to which the artifact affects recognition of the tissue feature in the first medical image. The processing device 120 may further determine whether the degree outputted by the determination model meets the preset condition.

In some embodiments, after the first medical image is acquired, the processing device 120 may determine whether the first medical image satisfies a preset condition before starting to acquire medical images when the target object is on other positions. In some embodiments, after the first medical image is acquired, the processing device 120 may determine whether the first medical image satisfies the preset condition within a predetermined time, wherein the predetermined time may be less than an estimated acquisition time. The estimated acquisition time may be obtained by collecting historical acquisition records, for example, historical acquisition time of scanning a target object of each of a plurality of users once, and an average time of the historical acquisition times may be designated as the estimated acquisition time.

The determining the degree to which the artifact in the medical image affects recognition of the tissue feature may include the following operations.

In 822, the processing device 120 (e.g., the determination module 420) may extract a feature of the medical image, and the feature may include a HOG feature of the medical image.

Detailed descriptions regarding the feature extraction of the medical image may refer to FIG. 6 and the relevant descriptions thereof, and not repeated herein.

In 824, the processing device 120 (e.g., the determination module 420) may input the HOG feature of the medical image into the determination model to determine the degree to which the artifact in the medical image affects recognition of the tissue feature.

Compared with a deep learning model, a shallow learning model may have fewer layers, and the number or count of training samples used to train the shallow learning model may be relatively less. In other words, the shallow learning model may converge the loss function based on a less amount of training samples. The shallow learning model may need less training data and have a fast training speed. Further, a trained shallow learning model may take less time to perform the evaluation. Therefore, the shallow learning model may be more suitable for a scenario that needs fast speed and less time for valuation.

As mentioned above, the acquisition and determination of the medical image may be real-time. To ensure that the determination model can determine the first image in real time after acquiring the first image, in some embodiments, the determination model may include a shallow learning model, e.g., an SVM model, a Logistic Regression model, a Naive Bayes classification model, or a decision tree model.

In 830, the processing device 120 (e.g., the acquisition module 410) may acquire a second medical image in response to a determination that the degree does not satisfy the preset condition.

A second medical image refers to a reacquired image of the target object when the target object is on the current position. Acquirement parameters of the imaging device 110 and the positions of the target objects may be same correspondingly when the imaging device 110 acquires the first medical image and the second medical image.

When a result outputted by the determination model satisfies the preset condition, the acquired medical image may be further processed, for example, the imaging device 110 may acquire another medical image of the target object when the target object is on another position.

In some embodiments, when the result outputted by the determination model does not satisfy the preset condition, the imaging device 110 may reacquire the second medical image in real time when the target object is on the current position. Further, the second medical image may be evaluated in real time. Until a medical image acquired when the target object is on the current position satisfies the preset condition, the imaging device 110 may acquire another medical image when the target object is on another position. In some embodiments, when a determination result outputted by the determination model does not satisfy the preset condition, the imaging device 110 may reacquire the second medical image at the current position after a portion of or all of the medical images are acquired when the target object is on other positions.

In some embodiments, when the preset condition is not satisfied, the imaging device 110 or the terminals 130 may issue a reminder to remind a manual intervention. For example, an operator may determine whether to rescan the target object at the current position.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A system for evaluating a medical image, comprising:
at least one storage device including a set of instructions; and
at least one processor configured to communicate with the at least one storage device, wherein when executing the set of instructions, the at least one processor is configured to direct the system to perform operations including:
obtaining the medical image;
extracting a feature of an artifact in the medical image, wherein the feature comprises a histogram of oriented gradients (HOG) feature of the medical image; and
determining an image quality of the medical image by inputting the feature of the artifact in the medical image to a determination model,
wherein extracting the feature of the artifact in the medical image includes:
calculating a gradient of each pixel in the medical image;
segmenting the medical image into a plurality of cell units, each of the plurality of cell units including a same count of pixels;
counting a HOG feature of each of the plurality of cell units based on the gradient of each pixel in each of the plurality of cell units;
combining the plurality of cell units into one or more blocks according to a predetermined number, and counting a HOG feature of each of the one or more blocks based on one or more HOG features of one or more cell units included in each of the one or more blocks; and
obtaining a HOG feature of the medical image by stitching the HOG features of the one or more blocks.

2. The system of claim 1, wherein the operations further comprise:
before stitching the HOG features of the one or more blocks, normalizing the HOG feature of each of the one or more blocks.

3. The system of claim 1, wherein the operations further comprise a process for obtaining the determination model, and the process comprises:
obtaining a plurality of sample medical images and a label of each of the plurality of sample medical images, wherein the label represents a degree to which an artifact in each of the plurality of sample medical images affects the tissue feature recognition;
extracting a feature of each of the plurality of sample medical images; and
obtaining the determination model by training a preliminary determination model based on the extracted feature and the label of each of the plurality of sample medical images.

4. The system of claim 3, wherein the process further comprises:
preprocessing each of the plurality of sample medical images, wherein the preprocessing includes: regularizing a size of each of the plurality of sample medical images and/or standardizing a color of each of the plurality of sample medical images.

5. The system of claim 3, wherein the operations further comprise:
obtaining additional determination models corresponding to different tissue types, wherein each of the determination models is obtained based on a plurality of sample medical images including a tissue type corresponding to the each of the determination models.

6. The system of claim 5, wherein the operations further comprise:
determining a tissue type included in the medical image;
obtaining a determination model corresponding to the tissue type; and determining the degree to which the artifact in the medical image affects recognition of the tissue feature by inputting the feature of the medical image to the determination model corresponding to the tissue type.

7. The system of claim 1, wherein the feature further comprises a gender and an age of a user from whom the medical image is acquired, and/or a tissue type of the medical image.

8. The system of claim 1, wherein the determination model is a support vector machine model, a logistic regression model, a naive Bayes classification model, a decision tree model, or a deep learning model.

9. A system for medical image acquisition, comprising:
at least one storage device including a set of instructions; and
at least one processor configured to communicate with the at least one storage device, wherein when executing the set of instructions, the at least one processor is configured to direct the system to perform operations including:
acquire a first medical image and conduct a determination process in real time, wherein the determination process comprises:
extracting a feature of an artifact in the first medical image, wherein the feature comprises a histogram of oriented gradients (HOG) feature of the first medical image;
determining an image quality of the medical image by inputting the feature of the artifact in the first medical image to a determination model; and
determining whether the degree satisfies a preset condition, and acquiring a second medical image in response to a determination that the degree does not satisfy the preset condition,
wherein extracting the feature of the artifact in the medical image includes:
calculating a gradient of each pixel in the medical image;
segmenting the medical image into a plurality of cell units, each of the plurality of cell units including a same count of pixels;
counting a HOG feature of each of the plurality of cell units based on the gradient of each pixel in each of the plurality of cell units;
combining the plurality of cell units into one or more blocks according to a predetermined number, and counting a HOG feature of each of the one or more blocks based on one or more HOG features of one or more cell units included in each of the one or more blocks; and
obtaining a HOG feature of the medical image by stitching the HOG features of the one or more blocks.

10. The system of claim 9, wherein the determination model is a shallow learning model including a support vector machine model, a logistic regression model, a naive Bayes classification model, or a decision tree model.

11. A method for evaluating a medical image, comprising:
obtaining the medical image;
extracting a feature of an artifact in the medical image, wherein the feature comprises a histogram of oriented gradients (HOG) feature of the medical image; and
determining an image quality of the medical image by inputting the feature of the artifact in the medical image to a determination model,
wherein extracting the feature of the artifact in the medical image includes:
calculating a gradient of each pixel in the medical image;
segmenting the medical image into a plurality of cell units, each of the plurality of cell units including a same count of pixels;
counting a HOG feature of each of the plurality of cell units based on the gradient of each pixel in each of the plurality of cell units;
combining the plurality of cell units into one or more blocks according to a predetermined number, and counting a HOG feature of each of the one or more blocks based on one or more HOG features of one or more cell units included in each of the one or more blocks; and
obtaining a HOG feature of the medical image by stitching the HOG features of the one or more blocks.

12. The method of claim 11, further comprising:
before stitching the HOG features of the one or more blocks, normalizing the HOG feature of each of the one or more blocks.

13. The method of claim 11, wherein a process for obtaining the determination model comprises:
obtaining a plurality of sample medical images and a label of each of the plurality of sample medical images, wherein the label represents a degree to which an artifact in each of the plurality of sample medical images affects the tissue feature recognition;
extracting a feature of each of the plurality of sample medical images; and
obtaining the determination model by training a preliminary determination model based on the extracted feature and the label of each of the plurality of sample medical images.

14. The method of claim 13, further comprising:
preprocessing each of the plurality of sample medical images, wherein the preprocessing includes: regularizing a size of each of the plurality of sample medical images and/or standardizing a color of each of the plurality of sample medical images.

15. The method of claim 13, further comprising:
obtaining additional determination models corresponding to different tissue types, wherein each of the determination models is obtained based on a plurality of sample medical images including a tissue type corresponding to the each of the determination models.

16. The method of claim 15, further comprising:
determining a tissue type included in the medical image;
obtaining a determination model corresponding to the tissue type; and
determining the degree to which the artifact in the medical image affects recognition of the tissue feature by inputting the feature of the medical image to the determination model corresponding to the tissue type.

17. The method of claim 11, wherein the feature further comprises a gender and an age of a user from whom the medical image is acquired, and/or a tissue type of the medical image.

18. The method of claim 11, wherein the determination model is a support vector machine model, a logistic regression model, a naive Bayes classification model, a decision tree model, or a deep learning model.

* * * * *